United States Patent [19]

Dwyer

[11] 4,107,224
[45] Aug. 15, 1978

[54] MANUFACTURE OF ETHYL BENZENE
[75] Inventor: Francis G. Dwyer, West Chester, Pa.
[73] Assignee: Mobil Oil Corporation, New York, N.Y.
[21] Appl. No.: 767,855
[22] Filed: Feb. 11, 1977
[51] Int. Cl.² .............................................. C07C 3/52
[52] U.S. Cl. .............................. 260/671 R; 260/671 C
[58] Field of Search ......................... 260/671 R, 671 C
[56] References Cited
U.S. PATENT DOCUMENTS 3,436,432  4/1969  Mitsche ........................... 260/671 R
3,542,892  11/1970 Stoker et al. .................... 260/671 R
3,751,504  8/1973  Keown et al. ................... 260/671 R
4,016,218  4/1977  Haag ............................... 260/671 R Primary Examiner—Delbert E. Gantz
Assistant Examiner—C. E. Spresser
Attorney, Agent, or Firm—Charles A. Huggett; Michael G. Gilman; Raymond W. Barclay

[57] ABSTRACT

Benzene and dilute ethylene are reacted in vapor phase over solid porous catalyst such as zeolite ZSM-5 in a series of reaction zones with intermediate injection of cold reactants and diluent to control temperature.

4 Claims, 1 Drawing Figure

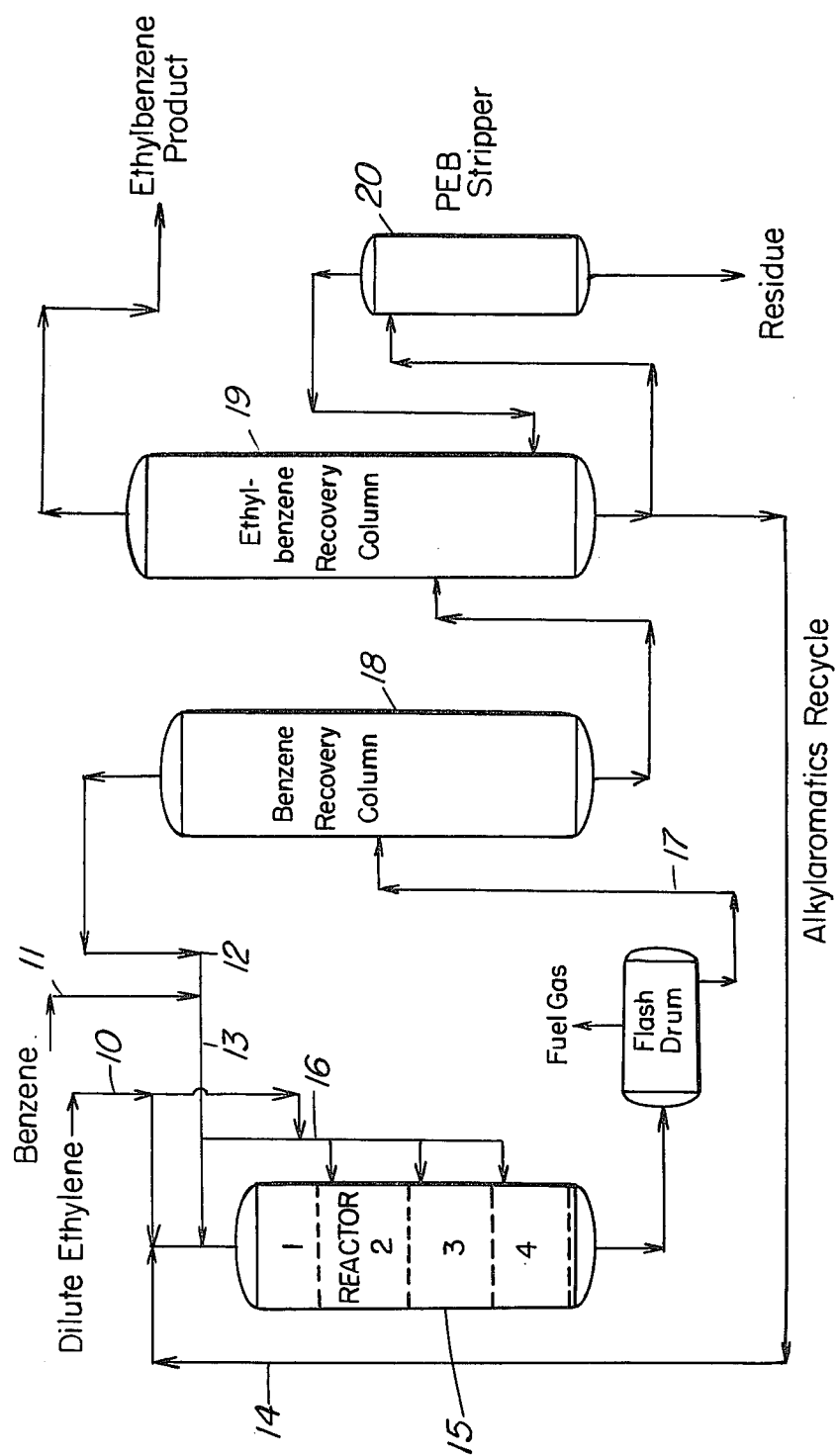

MANUFACTURE OF ETHYL BENZENE

BACKGROUND OF THE INVENTION

The large quantities of sytrene required by industry are derived by dehydrogenation of ethyl benzene, supplied in part by fractional distillation of hydrocarbon fractions of eight carbon atom aromatics such as those separated from catalytic reformates. The other primary source of ethyl benzene is from alkyalation of benzene, usually with ethylene. The commercial alkylation plants presently in operation employ catalysts of the Friedel-Crafts type, usually aluminum chloride. The liquid catalyst of that type in a stirred reactor makes it possible to remove the heat of reaction by conventional techniques.

The Friedel-Crafts catalysts are highly corrosive and require that reactors, heat exchangers and other auxiliaries by fabricated from expensive corrosion-resistant materials. The spent catalyst and other waste from such plants present a troublesome pollution problem. In addition, the reactants must be very pure to avoid undesirable by-products. In an adaptation of Friedel-Crafts catalyst to the use of catalytic cracking tail gas as source of ethylene for alkylation of benzene, all possibly reactive components other than ethylene must be scrupulously excluded. Hydrogen sulfide, carbon dioxide and water normally present in such tail gas are removable at little cost by caustic scrubbing to absorb the acidic gases hydrogen sulfide and carbon dioxide and by condensation of the water contained in the tail gas or picked up during scrubbing. Carbon monoxide requires much more expensive technique, but obviously must be removed before the gas is brought into contact with a Friedel-Crafts catalyst.

It will be immediately apparent that much of the disadvantage of Friedel-Crafts catalyst will be avoided by the use of a solid heterogeneous catalyst. Many solid porous catalysts having acid character have been shown to be active for the reaction of ethylene with benzene to synthesize ethyl benzene. Typically, the charge to such reaction will be a mixture in which the mole ratio of benzene to ethylene is high enough to suppress the formation of polyethyl benzenes and such amounts of these by-products as may be formed are subjected to transalkylation with benzene, either in the alkylation reactor or in a separate vessel. The acid catalysts are effective for promotion of polymerization. Some alkyl benzenes having larger side chains than ethyl can be found in the product. In addition the activity of the catalyst declines very rapidly, possibly due to formation of high molecular weight compounds which remain on the catalytic surfaces.

It has been shown that zeolites in the nature of zeolite ZSM-5 show high activity and selectivity for alkylation of benzene with ethylene and that catalysts of this type in the acid form remain active for unusually long periods between regenerations to burn off carbonaceous deposits which render the catalyst ineffective. Good discussion of acid zeolite ZSM-5 for this purpose is provided in U.S. Pat. No. 3,751,506, granted Aug. 7, 1973 on an application of George T. Burress. That patent proposes control of the exothermic heat of reaction by conducting the reaction is a series of reactors with intermediate cooling and addition of ethylene between stages. Note is there made that the course of the reaction may be affected by diluents and examples are given in which nitrogen is added in an amount equal to 0.5 mole per mole of ethylene.

SUMMARY OF THE INVENTION

According to the present invention, a reaction mixture of benzene and ethylene is charged to a series of alkylation reactors containing catalyst such as acid zeolite ZSM-5. In addition to the excess of benzene over the stoichiometric value for reaction with ethylene content of the charge, the ethylene is diluted by inert hydrocarbons in an amount greater than equi-molar quantity. Cooling between stages is accomplished by injection of the charge mixture at low temperature, preferably only slightly above the boiling point of benzene at the partial pressure of benzene in the charge mixture as introduced. Activity of the catalyst as measured by conversion of ethylene is very high, catalyst life is prolonged and selectivity to ethyl benzene plus diethyl benzene is excellent under these conditions.

DESCRIPTION OF THE DRAWING

A suitable flow diagram for accomplishing the stated objects of the invention is set out in the single FIGURE of the annexed drawing.

DESCRIPTION OF PREFERRED EMBODIMENTS

In practising the present invention, ethylene is supplied in a diluted form, preferably as a mixture with inert gaseous materials in which ethylene constitutes about 15 to 20 weight percent. A convenient source of such dilute ethylene exists in many oil refineries as tail gas from many units, for example from Fluid Catalytic Cracking (FCC). Typically such tail gases are used as refinery fuel after treating to remove hydrocarbons saleable as components of premium products such as bottled gas (LPG), gasoline or as charge for such process units as alkylation. In addition, the fuel gas is treated to remove the acidic gases hydrogen sulfide which causes pollution of stack gases and carbon dioxide which has no fuel value. It is a particularly valuable feature of the present invention that unreacted inert components of the ethylene diluting medium are fuel gas and may be easily separated from the crude product. The dilute ethylene stream for practice of the present invention requires only the same pretreatment as does fuel gas, whereby the pretreatment of the gas for practice of the invention also prepares the gas to the extent needed for fuel gas use. Note particularly that removal of carbon monoxide, a valuable fuel component, is unnecessary and this gas may be used in the process as diluent and then passed on for fuel use.

The principal diluents are the hydrocarbons methane and ethane, which will be present in an aggregate amount greater than the quantity of ethylene. Other diluents include hydrogen, nitrogen and carbon monoxide. Carbon dioxide is also a diluent and may be retained in the stream if desired, however it is readily removed with treatment to remove hydrogen sulfide and is preferably taken out to upgrade off-gas from the process for fuel use. Water and hydrogen sulfide are tolerable if more rapid aging of the catalyst is acceptable, but these are moderately detrimental in the process and must be removed in any event before supply of the off-gas to furnaces and the like.

A suitable dilute ethylene stream for use in process is prepared by scrubbing tail gas from the usual gas plant of an FCC Unit with aqueous caustic to remove hydrogen sulfide and carbon dioxide. The washed gas is cooled to condense water and any residual hydrocarbons of more than two carbon atoms. The treated gas had the following composition.

| methane | 37 vol % |
|---|---|
| ethane | 19 |
| ethylene | 19 |
| hydrogen | 9 |
| nitrogen | 13 |
| carbon monoxide | 3 |
| | 100 |

The said dilute ethylene stream was supplied by line 10 to apparatus shown diagramatically in the drawing. Fresh benzene entered the system at line 11 to mix with recycle benzene from line 12 and provide a blended stream of benzene in line 13. One portion of the dilute ethylene stream is mixed with polyalkyl aromatics recycled by line 14 and the blend is mixed with a portion of the benzene from line 13 to provide an aromatics to ethylene ratio by weight of 70. That mixture is admitted to stage 1 of a reactor 15 at 260 pounds per square inch gauge (psig) and 785° F.

The reactor 15 is provided with four beds of HZSM-5, each designated as a "stage" with plenum chambers between the beds for introduction of cool reactants.

The balance of the dilute ethylene from line 10 and the balance of the benzene from line 13 are mixed in pipe 16 and supplied in three portions to the plenum chambers following stages 1, 2 and 3 to cool effluent from the preceding stage to about 785° F. and supply fresh reactants. In each stage the temperature rises to about 820° F. due to the exothermic nature of the reaction.

Effluent from stage 4 of reactor 15 is cooled and passed to a flash drum 16 from which unreacted diluent is withdrawn to be used as fuel. Condensate from drum 16 is then passed by line 17 to a benzene recovery fractionator 18 from which unreacted benzene is taken overhead to line 12 for recycle as described. Bottoms from fractionator 18 are transferred to fractionator 19 from which ethyl benzene is taken overhead as product at line 20. The bottoms from fractionator 19 are transferred in part to a stripper 20 from which polyethyl benzenes are taken overhead and returned to fractionator 19. Materials heavier than polyethyl benzene are rejected as bottoms from stripper 20. The main stream of bottoms from fractionator is returned by line 14 to the inlet of reactor 15 where the polyethyl benzenes undergo transalkylation reactions with benzene.

The crude ethyl benzene product taken overhead from fractionator 19 had the following composition:

| $C_6$ non-aromatics | 0.005 wt. % |
|---|---|
| benzene | 2.345 |
| toluene | 0.254 |
| ethyl benzene | 97.166 |
| p-xylene | 0.090 |
| m-xylene | 0.102 |
| styrene | 0.010 |
| o-xylene | 0.016 |
| $C_9^+$ | 0.012 |
| | 100.000 |

It will be readily apparent to those skilled in the art that benzene and toluene can be reduced to very low levels by redistillation to provide ethyl benzene at better than 99.5% purity. The yield, based on ethylene consumed is 99.5% by weight at weight hourly space velocity (based on ethylene) of 5.

The zeolite catalysts utilized are members of a novel class of zeolites exhibiting some unusual properties. The zeolites induce profound transformations of aliphatic hydrocarbons to aromatic hydrocarbons in commercially desirable yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These zeolites retain their crystallinity for long periods in spite of the presence of steam at high temperatures which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conducive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framewrok of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e. they exhibit "hydrophobic" properties. It is belived that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these zeolites ineffective. Twelve-membered rings do not generally appear to offer sufficient constraint to produce the advantageous conversions, although puckered structures exist such as TMA offretite which is a known effective zeolite. Also, structures can be conceived, due to pore blockage or other cause, that may be operative.

Rather than attempt to judge from crystal structure whether or not a zeolite possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1. After 20 minutes on stream, a sample of the effluent is taken and analyzed, most conveniently by gas chromotography, to determine the fraction remaining unchanged for each of the two hydrocarbons.

The "constraint index" is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Zeolites suitable for the present invention are those having a constraint index in the approximate range of 1 to 12. Constraint Index (CI) values for some typical zeolites are:

| CAS | C.I. |
|---|---|
| ZSM-5 | 8.3 |
| ZSM-11 | 8.7 |
| ZSM-12 | 2 |
| ZSM-38 | 2 |
| ZSM-35 | 4.5 |
| TMA Offretite | 3.7 |
| Beta | 0.6 |
| ZSM-4 | 0.5 |
| H-Zeolon | 0.4 |
| REY | 0.4 |
| Amorphous Silica-Alumina | 0.6 |
| Erionite | 38 |

It is to be realized that the above constraint index values typically characterize the specified zeolites but that such as the cumulative result of several variables used in determination and calculation thereof. Thus, for a given zeolite depending on the temperature employed within the aforenoted range of 550° F. to 950° F., with accompanying conversion between 10% and 60%, the constraint index may vary within the indicated approximate range of 1 to 12. Likewise, other variables such as the crystal size of the zeolite, the presence of possible occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with probability, in some instances, of compounding variable extremes. However, in all instances, at a temperature within the above-specified range of 550° F. to 950° F., the constraint index will have a value for any given zeolite of interest herein within the approximate range of 1 to 12.

The class of zeolites defined herein is exemplified by ZSM-5, ZSM-11, ZSM-12, ZSM-35, ZSM-38 and other similar materials. U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-38 is more particularly described in U.S. application Ser. No. 528,060, filed Nov. 29, 1974. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)M_2O : Al_2O_3 : xSiO_2$$

wherein R is an organic nitrogen-containing cation derived from a 2-hydroxyalkyl) trialkylammonium compound, wherein alkyl is methyl, ethyl or a combination thereof, M is an alkali metal, especially sodium, and x is from greater than 8 to about 50.

The synthetic ZSM-38 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33Å.

TABLE I

| d (A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-38 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-38 (after calcination at 600° C.) is less than 10, whereas that ratio for the natural ferrierite is substantially greater than 10, for example, as high as 34 or higher.

Zeolite ZSM-38 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2 - 1.0 | 0.3 - 0.9 |
| OH⁻/SiO₂ | 0.05 - 0.5 | 0.07 - 0.49 |
| H₂O/OH⁻ | 41 - 500 | 100 - 250 |
| SiO₂/Al₂O₃ | 8.8 - 200 | 12 - 60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230° F. for from about 8 to 24 hours.

ZSM-35 is more particularly described in U.S. application Ser. No. 528,061, filed Nov. 29, 1974. This zeolite can be identified, in terms of mole ratios of oxides and in the anhydrous state, as follows:

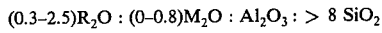
$(0.3-2.5)R_2O : (0-0.8)M_2O : Al_2O_3 : > 8\ SiO_2$ wherein R is an organic nitrogen-containing cation derived from ethylenediamine or pyrrolidine and M is an alkali metal cation, and is characterized by a specified X-ray powder diffraction pattern.

In a preferred synthesized form the zeolite has a formula, in terms of mole ratios of oxides and in the anhydrous state, as follows:

$(0.4-2.5)R_2O : (0.0.6)M_2O : Al_2O_3 : xSiO_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33Å. Close examination of some individual samples of ZSM-35 may show a very weak line at 11.3–11.5Å. This very weak line, however, is determined not to be a significant line for ZSM-35.

TABLE II

| d (A) | I/Io |
|---|---|
| 9.6 ± 0.2 | Very Strong–Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ration-hexane/2-methylpentane for ZSM-35 (after calcination at 600° C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, and organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2 - 1.0 | 0.3 - 0.9 |
| OH⁻/SiO₂ | 0.05 - 0.5 | 0.07 - 0.49 |
| H₂O/OH⁻ | 41 - 500 | 100 - 250 |
| SiO₂/Al₂O₃ | 8.8 - 200 | 12 - 60 | wherein R is an organic nitrogen-containing cation derived from pyrrolidine or ethylenediamine and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90° C. to about 400° C. for a period of time of from about 6 hours to about 100 days. A more preferred temperature range is from about 150° C. to about 400° C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230° F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-38 and ZSM-35, with ZSM-5, particularly preferred.

In a preferred aspect of this invention, the zeolites hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred zeolites of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structures. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Period Table, including, by way of example, nickel, copper, zinc, palladium, calcium or rare earth metals.

In practicing the desired conversion process, it may be desirable to incorporate the above described crystalline aluminosilicate zeolite in another material resistant to the temperature and other conditions employed in the process. Such matrix materials include synthetic or naturally occurring substances as well as inorganic materials such as clay, silica and/or metal oxides. The latter may be either naturally occurring or in the form of gelantinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix may vary widely with the zeolite content ranging from between about 1 to about 99% by weight and more usually in the range of about 5 to about 80% by weight of the composite.

Indications are that the catalyst will show very slow aging in this configuration. This conclusion is based on semi-commercial scale comparisons among adiabatic runs comparing alkylation of benzene over HZSM-5 with pure (polymer grade) ethylene and with ethylene diluted in the manner described above. Temperature probes in the adiabatic semicommercial reactor report a migration of the zone of maximum temperature downward through the down-flow reactor when charging polymer grade ethylene. The zone of maximum temperature is considered to be the zone of maximum (exothermic) reaction and it is concluded that catalyst ages as the zone moves downward. That effect is seen to a much lesser degree when charging the above-described dilute ethylene to the adiabatic reactor. Instead, the zone of maximum temperature in the catalyst bed remains quasi-stationary with a much lower rate of movement. This can lead logically to the conclusion that the catalyst is aging at a far less rapid rate.

The process of this invention is conducted such that alkylation of the aromatic hydrocarbon compound, benzene, with ethylene, is carried out in the vapor-phase by contact in a reaction zone under alkylation effective conditions, said catalyst being characterized as above zeolite which has been hydrogen exchanged such that a predominate portion of its exchangeable cations are hydrogen ions. In general, it is contemplated that more than 50% and preferably more than 75% of the cationic sites of the ZSM-5 zeolite will be occupied by hydrogen ions. The alkylatable aromatic compound and alkylating agent are desirably fed to a first stage at an appropriate mole ratio of one to the other. The feed to such first stage is heated. After reaction takes place, the effluent of the first stage is cooled to remove heat of reaction by addition of reactants. A plurality of reaction stages are possible for the process of this invention. It is generally desirable to provide cooling between reactor stages by addition of cool reactant.

In vapor-phase alkylation of benzene with ethylene, the first stage mole ratio of benzene to ethylene may be in the range of about 1:1 to about 30:1. The first stage feed is heated to a reactor inlet temperature within the range of about 650° F to about 900° F at a pressure within the range of about atmospheric to about 3000 p.s.i.g. Preferred inlet temperatures fall within the range of about 700° F to about 850° F and preferred pressures fall within the range of about 25 p.s.i.g. to about 450 p.s.i.g. The repeating of reaction staging is carried out while maintaining an overall aromatic hydrocarbon, e.g. benzene, to alkylating agent, e.g. ethylene, mole ratio of about 1:1 to about 30:1, with a preferred range of about 2.5:1 to about 25:1. As the reaction proceeds through the stages, the aromatic:alkylating agent mole ratio is held constant by changes in the ratio in the fresh interstage feed.

It is noted that extremely high total feed space velocities are possible in the process of this invention, i.e. up to 800 lb. total feed/hr-lb. crystalline aluminosilicate. An important factor in the present process is, however, the weight hourly space velocity (WHSV) of the alkylating agent, e.g. ethylene. The alkylating agent WHSV to each of any alkylation reactor stages is maintained between about 1 and about 10 lb. alkylating agent/hr-lb. crystalline aluminosilicate. The most desirable ethylene WHSV is within the range of about 2 to about 6 lb. ethylene/hr-lb. crystalline aluminosilicate. When the ethylene WHSV is maintained within the above limits, an economical cycle between regenerations of catalyst exists.

Operating in the manner described, run lengths of up to 29 days have been achieved, all terminated for reasons other than deactivation of the catalyst. It will be clear immediately that dilution of ethylene in the degree described increases the heat capacity of the system with resultant lower temperature rise across each catalyst bed. Also achieved is reduction in partial pressure of ethylene thus reducing polymerization of that olefin and subsequent formation of by-products such as butyl benzene. The inert hydrocarbons increase the partial pressure driving force to desorb coke precursors from the catalyst surface and thus reduce aging rate.

I claim:

1. In a process for effecting ethylation of an alkylatable aromatic hydrocarbon compound by contacting said compound with ethylene under conversion conditions of 250 to 600° C., a pressure between about 0.1 and about 100 atmospheres, a feed weight hourly space velocity between about 0.1 and about 100 and a molar feed ratio of said compound to ethylene between about 1 and about 30 in the presence of a crystalline aluminosilicate zeolite having a silica to alumina ratio of at least about 12 and a constraint index within the approximate range of 1 to 12 in a series of beds of said zeolite wherein effluent of each such bed except the last is admixed with fresh reactant supplied at a temperature lower than that of said effluent and the so-quenched reaction mixture is passed to the next such bed; the improvement comprises supplying charge to the first said bed and fresh reactants to said effluents as a mixture consisting essentially of said alkylatable aromatic hydrocarbon compound and ethylene admixed with at least an equi-molar amount of inert hydrocarbon diluent consisting essentially of methane, ethane or a mixture of the same whereby to increase the partial pressure driving force to desorb coke precursors from the catalyst surface.

2. The process of claim 1 wherein said alkylatable hydrocarbon is benzene.

3. The process of claim 1 wherein said crystalline aluminosilicate zeolite is ZSM-5.

4. The process of claim 1 wherein said crystalline aluminosilicate zeolite is admixed with a binder therefor.

* * * * *